United States Patent
Voix et al.

(10) Patent No.: US 12,413,920 B2
(45) Date of Patent: Sep. 9, 2025

(54) SYSTEM AND METHOD TO PERFORM IN-EAR NOISE DOSIMETRY AND PERSONAL ATTENUATION RATING UNDER AN ELECTRO-ACOUSTIC EARPLUG WHILE EXCLUDING WEARER-INDUCED DISTURBANCES AND SEPARATING EXPOSURE SOURCES

(71) Applicant: ECOLE DE TECHNOLOGIE SUPERIEURE, Montreal (CA)

(72) Inventors: Jeremie Voix, Montreal (CA); Antoine Bernier, Montreal (CA); Fabien Bonnet, Montreal (CA)

(73) Assignee: ECOLE DE TECHNOLOGIE SUPERIEURE, Montreal (CA)

( * ) Notice: Subject to any disclaimer, the term of this patent is extended or adjusted under 35 U.S.C. 154(b) by 629 days.

(21) Appl. No.: 17/758,988

(22) PCT Filed: Nov. 1, 2020

(86) PCT No.: PCT/CA2020/051481
§ 371 (c)(1),
(2) Date: Jul. 18, 2022

(87) PCT Pub. No.: WO2021/081671
PCT Pub. Date: May 6, 2021

(65) Prior Publication Data
US 2023/0035275 A1 Feb. 2, 2023

Related U.S. Application Data

(60) Provisional application No. 62/929,368, filed on Nov. 1, 2019.

(51) Int. Cl.
*H04R 29/00* (2006.01)
*A61F 11/08* (2006.01)
*G10K 11/178* (2006.01)

(52) U.S. Cl.
CPC .............. *H04R 29/00* (2013.01); *A61F 11/08* (2013.01); *G10K 11/17854* (2018.01)

(58) Field of Classification Search
CPC ....... H04R 29/00; H04R 1/1083; A61F 11/08; G10K 11/17854
See application file for complete search history.

(56) References Cited

U.S. PATENT DOCUMENTS 9,167,365 B2 * 10/2015 Voix ....................... H04R 25/70
2013/0094658 A1 4/2013 Holter
(Continued)

FOREIGN PATENT DOCUMENTS

| CA | 2477010 C | * | 7/2007 | .............. A61F 11/08 |
| WO | WO-2008061260 A2 | * | 5/2008 | ........... H04R 1/1016 |
| WO | WO-2008138349 A2 | * | 11/2008 | ........... G10K 11/178 |

OTHER PUBLICATIONS

Extended European Search Report dated Nov. 15, 2023, in the corresponding European Patent Application No. 20881596.9.
(Continued)

*Primary Examiner* — Oyesola C Ojo
(74) *Attorney, Agent, or Firm* — Brouillette Legal Inc.; Philippe Brouillette

(57) ABSTRACT

A system and method to measure noise reduction and evaluate the contributions of various sound sources to noise exposure dose of exposition using electro-acoustic earplugs is provided. The system may be implemented as an advanced HPD in the form of an electro-acoustical earplug. The earplug comprises an OEM 10 and an IEM. The system is configured to calculate an estimated IEM signal based on calculation of estimates of residual ambient noise, payback sounds or WID present in the ear canal.

15 Claims, 5 Drawing Sheets

(56) References Cited

U.S. PATENT DOCUMENTS

2016/0126914 A1* 5/2016 Voix .................. H03G 3/32
                                              381/57
2019/0075412 A1* 3/2019 Goldstein ............. H04R 3/007

OTHER PUBLICATIONS

International Search Report dated Jan. 13, 2021, International application No. PCT/CA2020/051481.

* cited by examiner

SYSTEM AND METHOD TO PERFORM IN-EAR NOISE DOSIMETRY AND PERSONAL ATTENUATION RATING UNDER AN ELECTRO-ACOUSTIC EARPLUG WHILE EXCLUDING WEARER-INDUCED DISTURBANCES AND SEPARATING EXPOSURE SOURCES

CROSS-REFERENCE TO RELATED APPLICATIONS

The present patent application claims the benefits of priority of U.S. Patent Application No. 62/929,368, entitled "SYSTEM AND METHOD TO PERFORM IN-EAR NOISE DOSIMETRY AND PERSONAL ATTENUATION RATING UNDER AN ELECTRO-ACOUSTIC EARPLUG WHILE EXCLUDING WEARER-INDUCED DISTURBANCES AND SEPARATING EXPOSURE SOURCES" and filed at the United States Patent and Trademark Office on Nov. 1, 2019, the content of which is incorporated herein by reference.

FIELD OF THE INVENTION

The present invention generally relates to methods and systems to measure the sound exposure under an electro-acoustic earplug as well as the personal attenuation rating (PAR) provided by the earplug. More specifically, the present invention relates to methods and systems for estimating the in-ear noise exposure from the earplug's receiver and/or the environment while excluding the noise contributions from the wearer (termed "wearer-induced disturbances). The present invention further relates to methods enabling estimation of the PAR, such as in the context of implementation on embedded computing platforms.

BACKGROUND OF THE INVENTION

Over 12% of the worldwide population is at risk of developing noise induced hearing loss (NIHL). Such proportion represents over 600 million of individuals, of which more than 22 million are North American workers exposed every day to noise exposure doses that put them at risk. Many workers use a variety of hearing protection devices (HPDs) to limit their exposure. Unfortunately, a given HPD can be a poorly suited choice, depending on the initial noise level that it attempts to reduce, if it under-attenuates and lets dangerous noise exposure dose still occur. Furthermore, a given HPD can be inadequate if it over-attenuates, leading to poor situational awareness and communication difficulties that may cause workers to occasionally remove of their HPDs while still subjected to high noise levels, leading to dangerous noise exposure dose. Even if an HPD is theoretically suitable, it can often be improperly fitted and underperform. Additionally, the background noise level may rise above expectations and make a previously suitable HPD no longer adequate.

Since residual noise level behind the hearing protector is generally unknown, the actual adequateness of the HPD at protecting the worker is generally unknown and, in some cases, the possibility of exposing workers to an excessive noise dose that may lead to permanent hearing damage cannot be ruled out. While in-situ estimation of the PAR helps in determining how the HPD actually performs on a given individual and can possibly assist in training individual to fit their HPD correctly, it is an incomplete solution if the residual noise exposure under the HPD is not considered.

As of now, ensuring that a given individual wearing HPDs does not exceed the recommended maximum noise exposure dose based on an 8-hours shift is difficult. In-ear noise dosimeters featuring an inner ear microphone (IEM) are starting to appear and allow measurement of the residual noise level under the HPD, but they have many limitations. First, they do not allow discrimination of wearer-induced disturbances (speech, chewing noise, etc.) that can contribute significantly to the measured in-ear sound pressure measured inside the occluded ear, notably due to the occlusion effect. While they contribute to in-ear SPL, it is possible that such disturbances may need to be treated differently than other sources due notably to the acoustic stapedius reflex, which reduces hearing sensitivity by up to 15 dB and has been shown to trigger when one speaks. Second, current in-ear dosimeters are not designed to be compatible with advanced hearing protection featuring an in-ear loudspeaker (IELS), which can be used for playback of communication and audio signals and, in combination with an outer ear microphone (OEM), can also be used to offer level dependent attenuation. Third, in-ear dosimeters do not allow segregation of the contribution of the various sound sources that contribute to the in-ear SPL, which can offer insight to come up with a suitable palliative strategy when the sound exposure limit is exceeded.

There is thus a need for a method or a system to measure the in-ear noise exposure under an advanced HPD while segregating the contributions of wearer-induced disturbances, communication and audio signals and level dependent attenuation.

SUMMARY OF THE INVENTION

The shortcomings of the prior art are generally mitigated by a system and method to measure the sound exposure under an electro-acoustic earplug while excluding wearer-induced disturbances.

In one aspect of the invention, a method to perform in-ear noise dosimetry and personal attenuation rating under an electro-acoustic earplug while excluding wearer-induced disturbances and separating exposure sources using models of electro-acoustical paths to separate the contributions of sound exposure from various sources and provide dosimetry is provided.

The method may further comprise applying different corrections, depending on the type of source, to each of separated contributions to obtain better accuracy by correcting the signals obtained at the IEM so that they better represent the signal that is inside the ear canal, at the inner-end of the ear tip.

In some aspects, the method may comprise using a FIR modeling the transfer function of the earpiece and a source signal provided by an OEM to estimate an IEM signal as a method for WID and playback segregation in the context of dosimetry.

In yet other aspects of the invention, the method may comprise using a FIR modeling of the transfer function between the loudspeaker and the IEM to filter incoming audio signal destined for playback as a method for WID and residual ambient segregation in the context of dosimetry.

The method may further comprise subtracting the estimates of an IEM signal as a method for WID and playback segregation in the context of dosimetry and residual ambient segregation in the context of dosimetry from the IEM to isolate the contribution of WID.

In some aspects of the invention, the method comprises strategies to manage WID contribution to sound exposure in the context of dosimetry, such as including it to the total dose, excluding it, weighting it, or any combination thereof.

In yet other aspects of the invention, the method further comprises temporarily weighting the contribution of all sources when significant WID energy is present to consider the effect of inhibition mechanisms such as the stapedius reflex, triggered by high level WID.

The method may also use the OEM and the IEM estimates to calculate a PAR in real-time that accounts for spectral uncertainty.

In another aspect of the invention, a system to measure noise reduction and evaluate contributions of various sound sources to a sound dose is provided. The system comprise a hearing protection device (HPD) comprising a passive attenuation device adapted to reduce ambient sound present outside an ear of a wearer of the HPD, an inner ear microphone (IEM) adapted to capture a general sound pressure level (SPL) of the sound dose present in the ear canal, outer ear microphone (OEM) adapted to capture the ambient sound, an in-ear loudspeaker (IELS) configured to emit a playback signal in an ear canal of a wearer according to at least one sound source. The system further comprising a processor in signal communication with the IEM and the OEM, the processor being configured to estimate at least one specific SPL corresponding to an identified sound component of the sound dose in the ear canal.

The processor may further be in signal communication with the IELS and the at least one specific SPL is a playback SPL, the processor being configured to compute an estimate value of the playback SPL according to the at least one sound source. The estimate value of the playback SPL may be computed according to at least one IELS-IEM model. The at least one IELS-IEM model may be an adaptive digital filter. The playback signal may be emitted according to a plurality of sound sources.

The at least one specific SPL may be a residual ambient SPL, the processor being configured to compute an estimate value of the residual ambient SPL according to the ambient sound captured by the OEM. The estimate value of the residual ambient SPL may be computed according to at least one passive attenuation model. The at least one passive attenuation model may be an adaptive digital filter. The processor may be further configured to subtract each of the at least one estimated specific SPL from the general SPL. The remainder of the subtraction may be an estimation of a wearer-induced disturbances (WID) SPL present in the ear canal.

The processor may be further configured to compute a correction for each of the at least one estimated specific SPL. The processor may be further configured to process each of the plurality of sound sources according to a corresponding one of the at least one IELS-IEM model. The plurality of sound sources may be at least one of an audio signal, a communication signal or a level-controlled output of the OEM. The HPD may further comprise an audio mixer adapted to combine the plurality of sound sources.

The HPD may further comprise a digital sound processor configured to receive the playback signal as input. The processor may be further configured to compute an OEM A-weighting according to the ambient sound captured by the OEM and to compute an estimated residual ambient A-weighting according to the estimated residual ambient SPL. The processor may be further configured to compute a personal attenuation rating (PAR) estimate by subtracting the estimated residual ambient A-weighting from the OEM A-weighting.

The system may further comprise a diagnostic module configured to receive the at least one estimated specific SPL. The diagnostic module may be configured to recommend at least one action to be executed by the wearer to reduce the sound dose in the ear canal.

In yet another aspect of the invention, a method to measure noise reduction and evaluate contributions of various sound sources of a sound dose in an ear canal of a wearer is provided. The method comprises capturing the sound dose in the ear canal, the sound dose comprising at least one sound component, estimating a specific canal SPL of the at least one sound component and subtracting the estimated specific canal SPL from the captured sound dose for each of the at least one sound component.

The method may further comprise capturing an ambient sound pressure level (SPL) outside the ear of the wearer and wherein the estimated specific canal SPL is an estimate of the residual ambient SPL present in the ear canal and the estimating is further performed according to the captured sound dose. The estimating may be further performed according to at least one passive attenuation model. The method may further comprise removing the estimated residual ambient SPL from the captured sound dose or may comprise determining an estimation of wearer-induced disturbances (WID) SPL present in the ear canal according to a remainder of the removing.

The method may further comprising emitting an IELS playback signal in the ear canal according to at least one sound source and wherein the estimated specific canal SPL is a playback SPL present in the ear canal and produced by the emitting. The estimating may be further performed by one or more IELS-IEM model. The IELS playback signal may be emitted according to a plurality of sound sources, the estimating comprising estimating one specific canal playback SPL for each of the plurality of sound sources. The estimating may be further performed by one or more IELS-IEM model for each of the plurality of sound sources signal. The method may comprise mixing the plurality of sound sources to generate the IELS playback signal or may comprise removing the estimated IELS playback SPL from the captured sound dose. The method may further comprise estimating of wearer-induced disturbances (WID) SPL present in the ear canal according to the removing. The method may further comprise digitally processing the emitted IELS playback signal.

The method may further comprise emitting an IELS playback signal in the ear canal according to at least one sound source, estimating the playback SPL present in the ear canal according to from the at least one sound sources, removing the estimated residual ambient SPL and the estimated playback SPL from the captured sound dose and estimating wearer-induced disturbances (WID) SPL present in the ear canal according to the removing.

The method may further comprise calculating an OEM A-weighting according to the captured ambient SPL and calculating a canal A-weighting according to the estimated residual ambient SPL. The method may further comprise calculating a personal attenuation rating (PAR) estimate by subtracting the canal A-weighting from the OEM A-weighting. The method may further comprise recommending at least one action to be executed by the wearer to reduce the sound dose in the ear canal according to the estimated specific canal SPL.

In a further aspect of the invention, a system to measure noise reduction and evaluate contributions of residual ambient sound pressure level (SPL) of a sound dose present in an ear canal is provided. The system comprises a hearing protection device (HPD) comprising a passive attenuation device adapted to reduce ambient sound present outside an ear of a wearer of the HPD, an inner ear microphone (IEM) adapted to capture canal sound pressure level (SPL) of the sound dose present in the ear canal, an outer ear microphone (OEM) adapted to capture the ambient sound. The system further comprises a processor in signal communication with the IEM and the OEM, the processor being configured to compute an estimate of the residual ambient SPL of the sound dose in the ear canal.

The estimate of the residual ambient SPL may be computed according to one or more passive attenuation models, the one or more passive attenuation models being determined according to the captured ambient sound. The one or more passive attenuation models may be an adaptive digital filter. The processor may be further configured to perform a subtraction of the estimate of the residual ambient SPL from the canal SPL. An estimation of wearer-induced disturbances (WID) SPL present in the ear canal may be determined according to the subtraction. A calibration of the one or more passive attenuation models may be performed according to the subtraction. The processor may be adapted to execute an adaptive algorithm to calibrate the one or more passive attenuation models according to the subtraction.

In another aspect of the invention, a system to measure noise reduction and evaluate contributions of a playback sound pressure level (SPL) of a sound dose present in an ear canal of a hearing protection device (HPD) wearer is provided. The HPD comprising an inner ear microphone (IEM) adapted to capture a canal sound pressure level (SPL) of the sound dose present in the ear canal, an in-ear loudspeaker (IELS) configured to emit a playback signal in the ear canal, according to at least one sound source. The system further comprising a processor in signal communication with the IEM and the IELS, the processor being configured to estimate a playback SPL according to the canal SPL.

The estimate of the playback SPL may be computed according to at least one IELS-IEM model, the at least one IELS-IEM model being determined according to the at least one sound source. The at least one IELS-IEM model may be an adaptive digital filter. The playback signal may be emitted according to a plurality of sound sources and wherein the processor is further configured to estimate the playback SPL for each of the plurality of sound sources. The processor may be further configured to perform a subtraction of the estimated playback SPL from the canal SPL. An estimation of wearer-induced disturbances (WID) SPL present in the ear canal may be determined according to the subtraction.

A calibration of the at least one IELS-IEM model may be performed according to the subtraction. An adaptive algorithm may be determined for the calibration, the adaptive algorithm being determined according to the subtraction.

Other and further aspects and advantages of the present invention will be obvious upon an understanding of the illustrative embodiments about to be described or will be indicated in the appended claims, and various advantages not referred to herein will occur to one skilled in the art upon employment of the invention in practice.

BRIEF DESCRIPTION OF THE DRAWINGS

The above and other aspects, features and advantages of the invention will become more readily apparent from the following description, reference being made to the accompanying drawings in which.

DETAILED DESCRIPTION OF THE PREFERRED EMBODIMENT

A novel method and system to measure noise reduction and evaluate the contributions of various sound sources to noise exposure dose of exposition using electro-acoustic earplugs will be described hereinafter. Although the invention is described in terms of specific illustrative embodiments, it is to be understood that the embodiments described herein are by way of example only and that the scope of the invention is not intended to be limited thereby.

Figure 1:
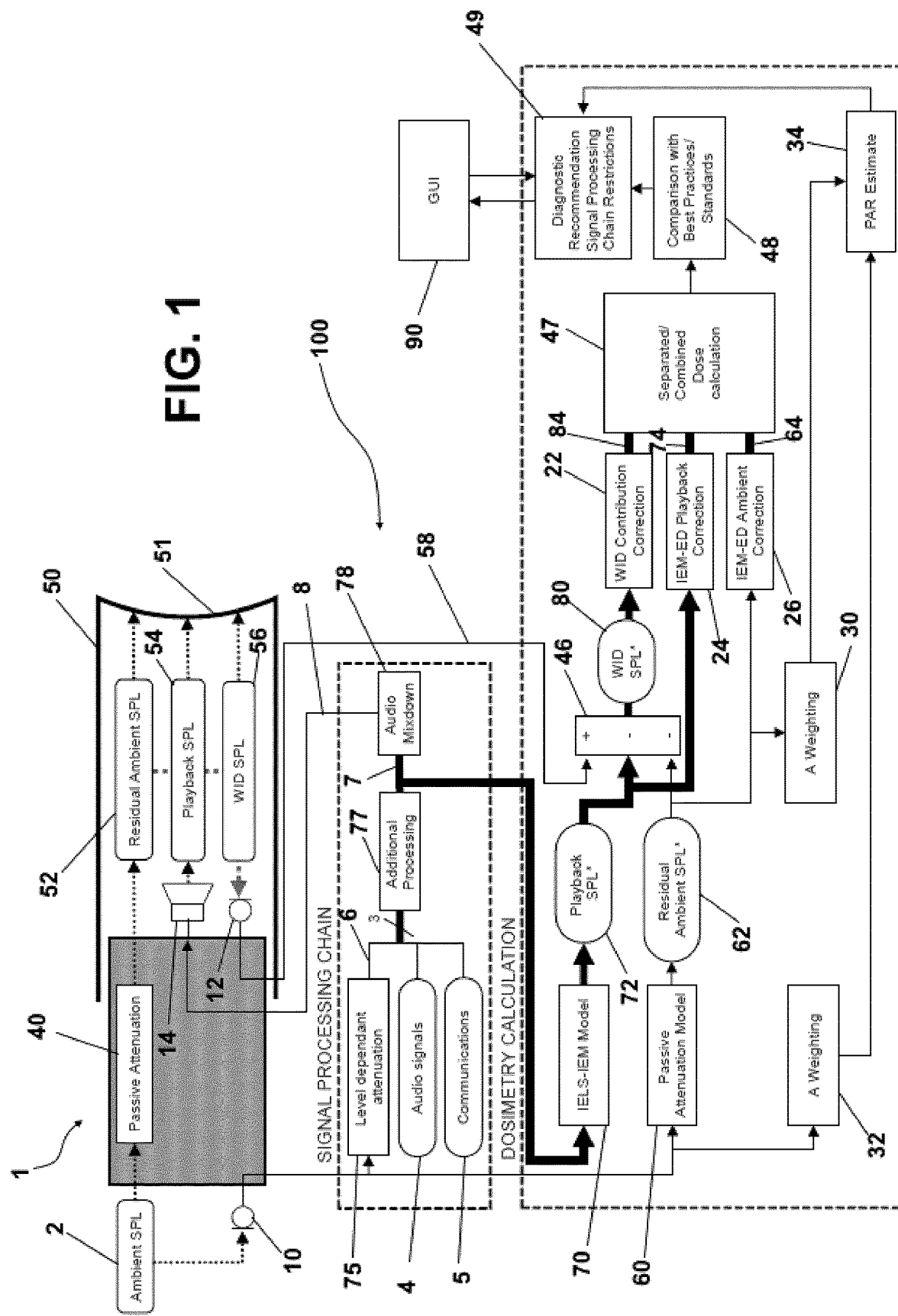
FIG. 1 is an illustration of a system to measure noise reduction and evaluate the contributions of various sound sources to noise exposure dose of exposition using electro-acoustic earplugs.

Now referring to FIG. 1, an embodiment of a system to measure noise reduction and evaluate the contributions of various sound sources to noise exposure dose of exposition using electro-acoustic earplugs 100 is illustrated. The system 100 may be implemented as an advanced HPD in the form of an electro-acoustical earplug. The earplug 1 comprises an OEM 10 and an IEM 12. In some embodiments, the earplug 1 may further comprise an IELS 14, generally adapted for playback of audio 4 and communication signals 5. The IELS 14 may be controlled to lower or increase the volume of sound emitted by the OEM 10, the audio 4 and communication signals 5. The earplug 1 may further comprise a processing device, such as a processor or a controller, and a memory unit allowing to store instructions to be executed or any data needed to execute the said instructions.

The audio 4 and communication 5 signals provide separated contributions to a noise dose received in the ear canal 50. The earplug 1 is configured to calculate estimates of the various electro-acoustical paths from sound sources to the inner end of the earplug using different models, such as models using adaptive filters.

In use, the HPD 1 is inserted into the ear canal 50 of a user. The HPD 1 may be configured to have audio playback 4 and/or communication 5 capabilities.

When worn by the user, a user's sound exposure or sound dose typically comprises three major classes of exposure sources: the residual ambient noise or sounds 52, sounds 4, 5 emitted by the IELS 14 and/or wearer-induced disturbances (WID) 56.

First, the ambient noise or sound 2 surrounding the ear of the user is attenuated by the HPD 1. The HPD 1 acts as a passive attenuation 40 resulting in in residual ambient noise or sound 52 present in the ear canal 50.

Second, the IELS 14 produces an audio playback 4, a communication signal 5 or any other audio signal. The IELS 14 is typically connected to the OEM 10 which captures the ambient sounds 2. A level dependent attenuation module 75 is configured to varies the level of the ambient sounds 2 captured by the OEM 10. In some embodiments, the level dependent attenuated signal 6, the audio signals 4 and/or the communication signals 5 may receive additional processing 77 to manipulate the inputted sounds sources through mathematic formulae or algorithms to output respective resulting signals 7.

The sounds from the different sources, such as the audio playback 4, a communication signal 5 and/or the level dependent attenuated signal 6, may be merged, combined or mixed prior to be emitted by the IELS 14. In some embodiments, the signals 4, 5 and/or 6 are mix using any mixing device 78. The resulting mix audio signal 8 is inputted in the IELS which is configured to emit the said signal 8 in the ear canal. The audio signal 8 contributes to the sound exposure or dose of the ear canal 50 in the form of playback sound 54.

Third, wearer-induced disturbances (WID) 56, such as talking, chewing or any other wearer inner sounds, contribute to the sound exposure in the form of bone-conducted acoustical signals 56 that are amplified by the occlusion effect present in the ear canal 50.

The IEM 12 of the HPD 1 is generally positioned in the ear canal 50 to capture the sound exposure or dose within the said ear canal 50. The output of the IEM 12 is the IEM sound pressure level (SPL) 58.

The HPD calculates an estimated playback SPL 72 in the ear canal 50 and calculates an estimated residual ambient SPL 62. In some embodiments, the HPD uses an IELS-IEM model 70 to calculate the estimated playback SPL 72 and a passive attenuation model 60 to calculate the estimated residual ambient SPL 62. The estimated playback SPL 72 and the estimated residual ambient SPL 62 are subtracted from the IEM SPL 58. The subtraction process 46 is typically executed using the processor or controller of the HPD 1. The resulting signal of the subtraction process 46 is an estimated WID SPL 80.

The resulting estimated SPL 62, 72 and 80 represents an estimation of the different components of the sound dose within the ear canal 50.

In some embodiments, the estimated ambient SPL 62 of the contribution of ambient noise 52 is calculated using a passive attenuation model 60. The passive attenuation models use the SPL captured by the OEM as input. The passive attenuation model 60 typically calculates a transfer function estimate of the noise reduction or attenuation of the HPD 1 using an adaptive digital filter. Such adaptive digital filter models the acoustical path between the OEM 10 and the IEM 12. Understandably, any known method to evaluate or to compute the attenuation of the HPD 1 may used within the scope of the present invention.

Figure 2:
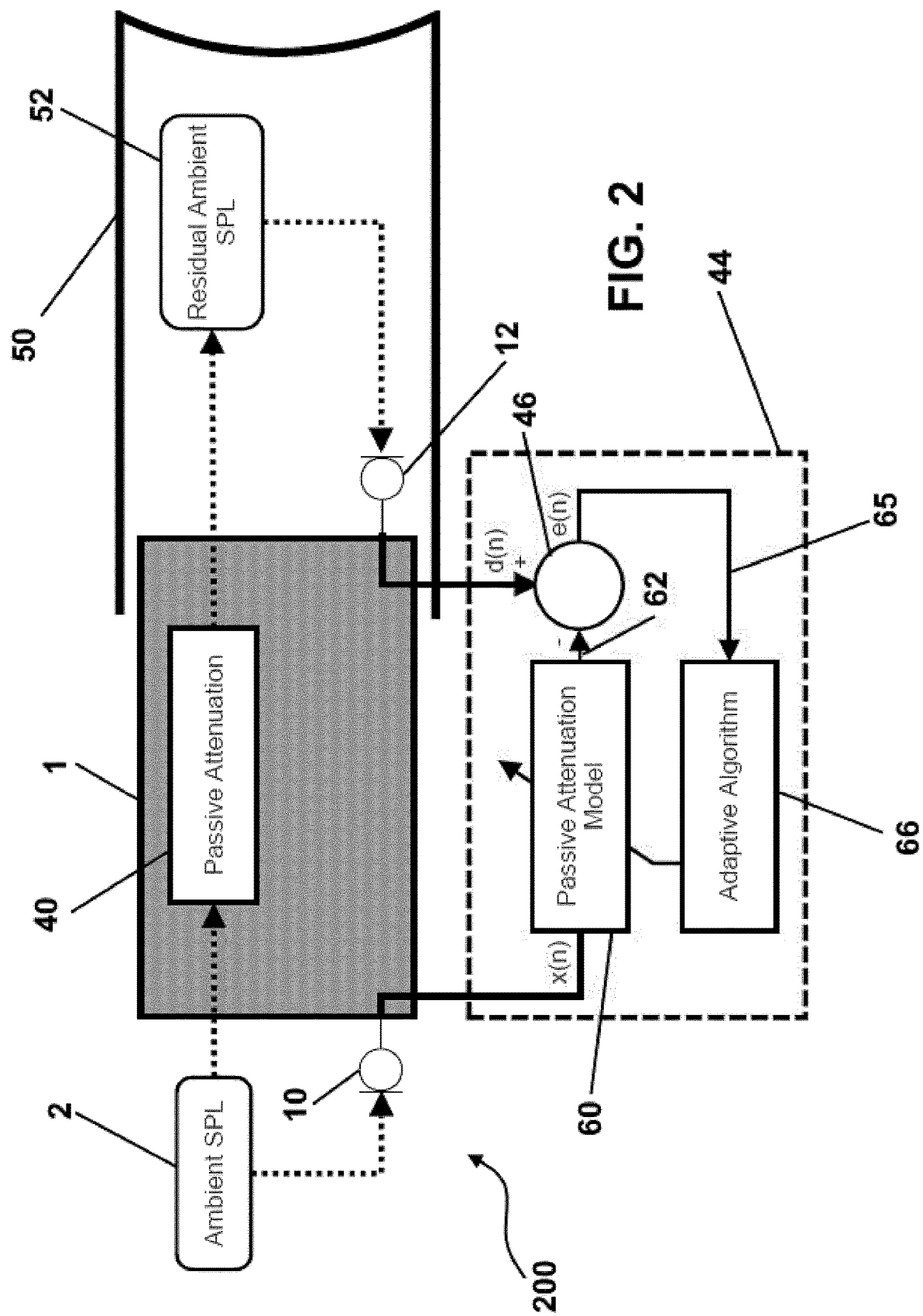
FIG. 2 a calibration phase/modeling phase of a passive attenuation model according to the principles of the present invention.

Referring now to FIG. 2, in some embodiments, the passive attenuation model 60 may be calibrated to offer a better estimate of the passive attenuation 40 of the HPD 1. In such embodiments, the adaptive filter is calibrated during an identification or calibration phase. In an exemplary embodiment, the identification phase comprises having ambient sounds being present in the ear canal 50. Typically, only residual ambient sounds 52 will be present in the ear canal 50 to obtain better calibration results. The residual ambient sounds 52 will be compared to the sounds captured by the OEM 10 to calibrate the passive attenuation model 60. Understandably, other known calibration methods to calculate the attenuation of the HPD may be used within the scope of the present invention.

This identification or calibration phase may be triggered manually, such as by the user or may be executed periodically at pre-determined time intervals, or executed upon predetermined conditions being detected. Suitable conditions may comprise, but are not limited to, high sound pressure levels being detected by the OEM 10 and low sound pressure levels being detected by the IEM 12. During calibration, the filter shall converge to a noise reduction model or value associated with the HPD 1. The calibrated filter is then executed to filter the OEM 10 signal which is dominated by ambient sound. During execution, the calibrated filter outputs an estimate 62 of the portion of sound energy present inside the ear canal 50 due to residual ambient noise 52 using the calculated noise reduction model or value.

Still referring to FIG. 2, the calibration phase/modeling phase 200 of the passive attenuation model 60 is illustrated. In such calibration/modeling period 200, an adaptive algorithm 66 uses the resulting signal e(n) 65 as input to update or recalculate the passive attenuation model 60. Typically, a known ambient SPL 2 captured by the OEM 10 x(n) is fed to the passive attenuation model 60. The estimated residual ambient SPL 62 is calculated and is subtracted 46 from the sound dose captured by the OIM 12. The resulting signal e(n) 65 is used by the adaptive algorithm to calibrate or update the model 60.

In yet other embodiments, the estimation of the contribution of playback sound 72 to sound exposure relies on a model of the transfer function of the electro-acoustical path from the input of the IELS 14 to the output of the IEM 12 using an IELS-IEM model 70, such as an adaptive digital filter. The TEL model 70 uses the digitally processed output signals 7 or the audio signals 4, the communications signal 5 and the level dependent attenuated signal 6 as different inputs. In some embodiments, the IELS-IEM model 70 calculates an estimate of each of the signals 4, 5, 6 to produce different playback SPL 72. Understandably, the present estimation may be configured to use a mixdown signal 8 of the audio signals 4, 5, 6 to output a single playback SPL 72.

Figure 3:
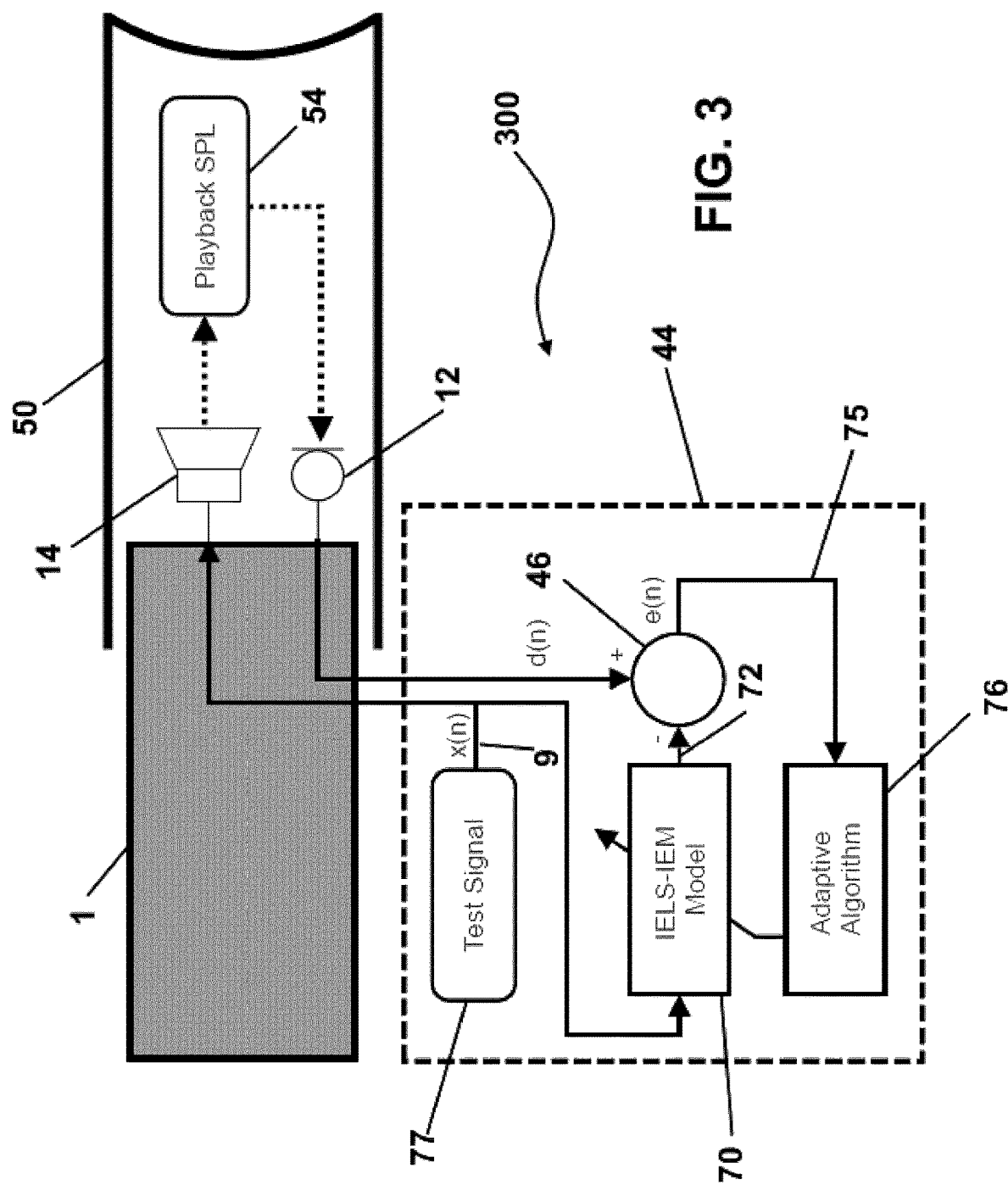
FIG. 3 a calibration phase/modeling phase of an IELS-IEM model according to the principles of the present invention.

Similarly to the passive attenuation model 60, as illustrated in FIG. 3, the filter within the model 70 may be calibrated during an identification or calibration phase. Such identification phase generally comprises the step of the IELS 14 producing a test signal 9 in the ear canal 50. The identification phase may be manually triggered, such as triggered by the user, may be automatically executed at pre-defined time intervals, or may be automatically executed when suitable conditions are detected. The suitable conditions may comprise, but are not limited to, any signals being currently played back through the IELS 14, while low sound pressure levels are detected by the OEM 10. In some embodiments, the estimation model or value may be provided to the filter of the model 70. As an example, the estimation model or value may be readily available from a communication earpiece adapted to provide echo cancellation. Echo cancellation is generally used to prevent echo in full-duplex communication systems. Echo cancellation generally relies on modeling the path between the input of the IELS 14 to the output of the OEM 10. The identification phase further comprises accurately calculating the estimation models by letting the filter of the model 70 converging to the estimation models and/or values of the electro-acoustical path between the IELS 14 and the IEM 12.

Still referring to FIG. 3, the calibration phase/modeling phase 300 of the IELS-IEM model 70 is illustrated. In such an embodiment, the system 100 further comprises an emitting device 77 for producing a test signal 9. The test signal 9 is emitted by the loudspeaker 14 in the ear canal and in the TEL model 70 at time of calibration. The IELS-IEM model 70 computes an estimate of the test signal 72 which is subtracted from the sound dose captured by the IEM 12. The resulting signal 75 (e(n)) is processed using an adaptive algorithm or instructions 76 to update or recalculate the IELS-IEM model 70. As explained above, the resulting signal 75 from the subtraction 46 may be corrected and used in a diagnostic module 49 or may be used during a calibration period.

The calibrated filter is used to filter incoming audio signals, either separately (audio prompts, music, communications, level dependant attenuation), or after combination into an overall audio signal, thereby obtaining an estimate 72 of the portion of sound energy present inside the ear canal 50 due to playback sounds or different estimates 72 for each components of the audio playback signals.

As discussed above, the estimation of the contribution of WIDs 56 is obtained by elimination or subtraction 46. From the IEM 12 signal, which measures all or most of the sounds present in the ear canal 50, the predefined portions of sound energy attributable to ambient residual noise 52 and playback sounds 54 may be removed, leaving the portion of sound energy present in the ear canal due to WIDs 56.

In some embodiments, the HPD or electro-acoustical earpiece 1 may comprise an ear tip having a sound channel (not shown) to which is coupled the IEM 12. In such embodiments, the IEM 12 is not directly located inside the ear canal 50, but rather acoustically coupled to the ear canal 50 through the sound channel. The ear tip or sound channel is adapted be sealingly fitted to the walls of the ear canal 50. Such seal generally aims at providing a hearing protection. Thus, the IEM 12 signal is not identical to that present inside the ear canal 50, at the inner end of the ear tip.

In such or in other embodiments, the HPD or electro-acoustical earpiece 1 may be configured to calculate a correction of the estimates SPL outputted by the filters 62, 72 and/or of the estimated WID SPL 80. In some embodiments, the correction may differ depending on whether the source of sound exposure is ambient noise 52, playback sound 54 and/or WIDs 56. A separate correction can therefore be used for each of these source classes, such as WID contribution correction 22, IEM playback correction 24 and/or IEM ambient correction 26. Such corrections 22, 24 and 26 are applied to the estimated SPL 62, 72 and 80 to obtain respective corrected signals 64, 74 and 84.

Understandably, these corrections 22, 24 and/or 26 can be pre-calculated using acoustical models, or pre-measured using calibration procedures, and applied separately to each estimated contributive signal to obtain a corrected estimation of the sound pressure level at the inner-end of the ear tip.

From the inner end of the ear tip to the eardrum 51, the transfer function is independent of the source and a single correction may be used.

The contribution of WIDs 56 to overall noise exposure is still being debated in the literature and, due to mechanisms like the stapedius reflex, may need to be included, reduced by a fixed or variable amount over time, completely excluded, or expressed separately. The present method allows for all these scenarios. In some embodiments, the method comprises temporarily applying one or more weightings in the dose calculation 47 to the contribution of all sources when WIDs 56 are present in significant amount.

In some embodiment, a personal attenuation rating (PAR) 34 may be estimated using the ambient SPL 2 provided by the OEM 10 and the estimate of the residual ambient SPL 62. In such embodiments, the HPD may be configured to calculate a first A-weighting value 32 of the ambient SPL 2. The HPD 1 is further configured to calculate a second A-weighting value 30 of the estimated residual ambient SPL 62. The HPD 1 is further configured to subtract the second A-weighting 30 from the first A-weighting 32 to obtain the PAR estimate 34. The PAR estimate 34 generally providers another parameter in the analysis of the estimated components 62, 72 and 80 of the sound dose in the ear canal 50.

The PAR estimate value 34 generally provides a continuous estimation of the IEM signal that is free of disturbances such as WID 56 or playback sounds 54 that can be used to estimate the PAR, and can capture variations in the PAR 34 that are due to variations in the spectral content of the ambient noise.

In some further embodiments, the estimated SPL 62, 72, 80 and/or corrected estimated SPL 64, 74, 84 may be inputted to a diagnostic module 49. The diagnostic module 49 may be configured to calculate suggestion or recommended actions for the user based on the different values of the inputted estimated SPL 62, 72, 80 and/or corrected estimated SPL 64, 74, 84. As examples, the diagnostic module 49 may suggest to a user to move to a calmer area as the total sound dose of the ear canal 50 exceeds a predetermined level and the weight of the estimated residual ambient SPL 62 exceed the weights of the other estimated components 72 or 80 or exceeds a predetermined level. In another example, the diagnostic module 49 may suggest to the user to reduce the sound of the audio signal 4 or to suggest reducing the number of calls producing the communication signal 5. In further other embodiments, the sound levels of the communication signals 5 or audio signals 4 may be automatically reduces when an overall SPL exceeds a predetermined value and the weights of such signal 4, 5 also exceed one or more predetermined levels.

In some embodiments, the system 100 may further comprise a module to calculate the dose in the ear canal 47 using as input the separated estimated sound dose components 62, 72, 80 and/or the corrected values 64, 74 or 84. The resulting values may be SPL of each of the components or combined values of each component.

In a further embodiment, the diagnostic module 49 may be fed by standard or best practices in dosimetry. In such embodiment, a comparison module 48 uses as input the separated and/or combined dose calculation 47 and compares the said dose calculation with the standard and best practices. The resulting value may be inference values or boolean values indicating if the said separated or combined doses are within the boundaries of the standard and/or best practices values.

Still referring to FIG. 1, in yet other embodiments, the system 100 may further comprise a graphical user interface (GUI) 90 adapted to communicate, display and/or read the suggestions or recommendations calculated by the diagnostic module 49. Understandably, any GUI 90 may be used such as displaying results on a mobile device or a computer, communicating the results through a network or using the loudspeaker 14 to read the suggestion to the wearer.

Another embodiment of the system 100 to measure noise reduction and evaluate the contributions of ambient sound within the ear canal of a wearer is illustrated. The system 100 comprises an OEM 10 and an IEM 12 within the ear canal 50. The system 100 comprises an earplug or attenuation device 1 having a form of passive attenuation 40, such as a plug. The system 100 further comprises a DSP or processing device 44, such as a processor or a controller, and may comprise a memory unit allowing to store instructions to be executed or any data needed to execute the said instructions.

The processing device 44 is configured to calculate and/or compute an estimate value 62 of the residual ambient SPL 52 present in the ear canal 50 based on the ambient SPL 2 captured by the OEM 10. The estimation is typically computed using a passive attenuation model 60, such as an adaptive digital filter.

The system 100 further comprises a subtraction module 46 adapted to subtract the estimated ambient SPL 62 from the sound dose captured by the IEM 12 within the ear canal 50. As explained above, the resulting signal containing the estimated WID SPL 80 from the subtraction 46 may be corrected and used in a diagnostic module 49.

Yet another embodiment of a system 100 to measure noise reduction and evaluate the contributions of playback sound within the ear canal of a wearer is illustrated. The system 100 comprises an IEM 12 within the ear canal 50 and an IELS 14, generally adapted for playback of audio 4 and communication signals 5, as shown in FIG. 1. The system 100 comprises an earplug or attenuation device, such as a plug. The system 100 further comprises a DSP or processing device 44, such as a processor or a controller, and may comprise a memory unit allowing to store instructions to be executed or any data needed to execute the said instructions.

As discussed above, the signals provide separated contributions to a noise dose received in the ear canal 50.

As previously discussed, the processing device 44 is configured to calculate and/or compute an estimate value 72 of the playback SPL 54 present in the ear canal 50 based on the playback source signal, such as audio 4 and communication 5 signals. The estimation is typically computed using an IELS-IEM model 70 for the combined signal 8 (see FIG. 1) or for each component, such as the audio signal 4 or the communication signal 5.

Figure 4:
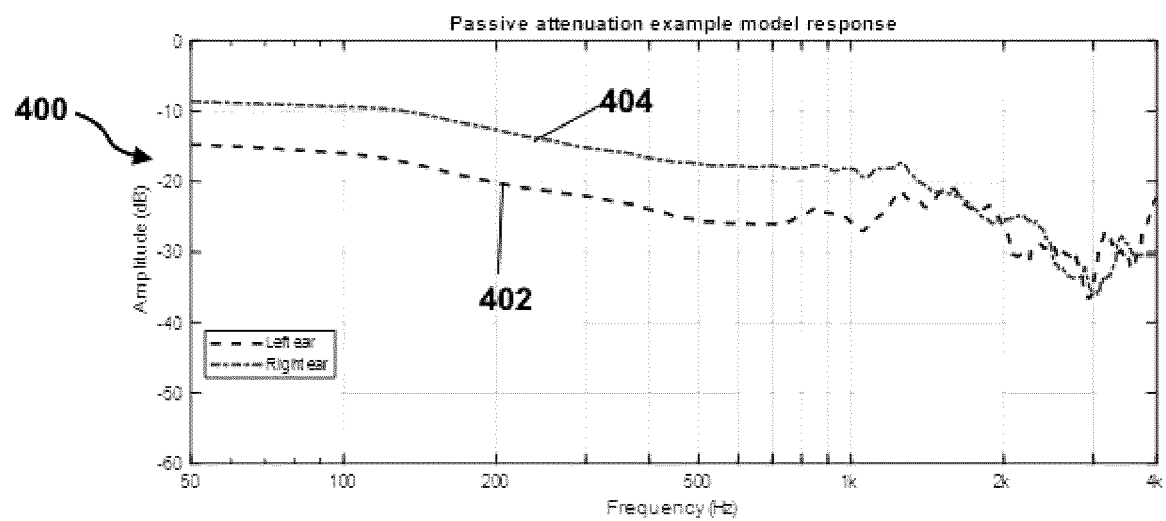
FIG. 4 is an example graph of an amplitude of a response of a passive attenuation model as a function of the frequency according to the principles of the present invention.

Referring now to FIG. 4, an example graph of the amplitude of the response of the passive attenuation model as a function of the frequency 400 is illustrated. The response for the left 402 and right 404 ears are illustrated.

Figure 5:
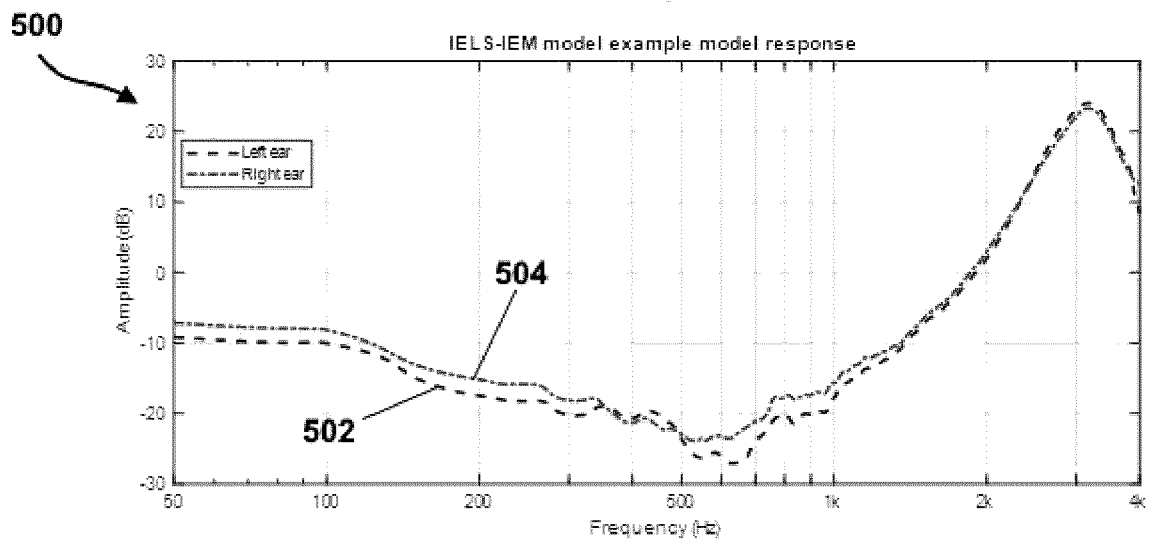
FIG. 5 is example graph of the amplitude of the response of an IELS-IEM model as a function of the frequency according to the principles of the present invention.

Referring now to FIG. 5, an example graph of the amplitude of the response of the IELS-IEM model as a function of the frequency 500 is illustrated. The responses for the left 502 and right 504 ears are illustrated.

Figure 6:
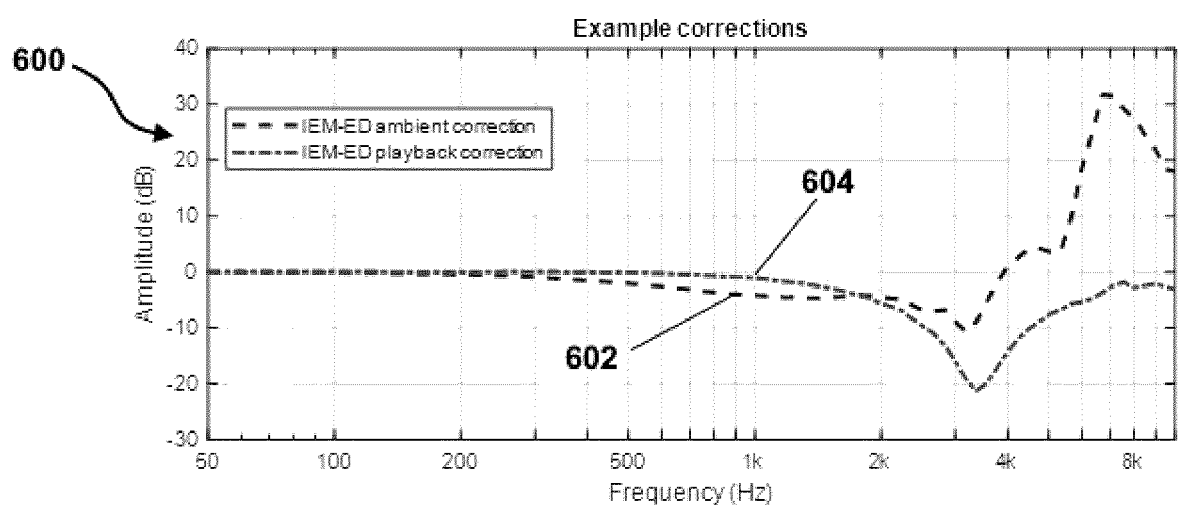
FIG. 6 is an example graph of the amplitude of the correction of a passive attenuation model and of an IELS-IEM model as a function of the frequency according to the principles of the present invention.

Referring now to FIG. 6, an example graph of the amplitude of the correction of the passive attenuation model 602 and of the IELS-IEM model 604 as a function of the frequency 600 is illustrated.

While illustrative and presently preferred embodiments of the invention have been described in detail hereinabove, it is to be understood that the inventive concepts may be otherwise variously embodied and employed and that the appended claims are intended to be construed to include such variations except insofar as limited by the prior art.

The invention claimed is:

1. A system to measure noise reduction and evaluate contributions of various sound sources to a sound dose, the system comprising:
    a hearing protection device (HPD) comprising:
        a passive attenuation device adapted to reduce ambient sound present outside an ear of a wearer of the HPD;
        an inner ear microphone (IEM) adapted to capture a general sound pressure level (SPL) of the sound dose present in the ear canal;
        at least one of an outer ear microphone (OEM) adapted to capture the ambient sound; and
        an in-ear loudspeaker (IELS) configured to emit a playback signal in an ear canal of a wearer according to at least one sound source;
    a processor in signal communication with the IEM and with at least one of the OEM and the IELS, the processor being configured to:
        estimate at least one specific SPL corresponding to an identified sound component of the sound dose in the ear canal using at least one model of a transfer function between the IEM and at least one of the OEM and the IELS; and
        subtract each of the at least one estimated specific SPL from the general SPL and wherein a remainder of the subtraction is an estimation of a wearer-induced disturbances (WID) SPL present in the ear canal.

2. The system of claim 1, wherein the at least one specific SPL is a playback SPL, the processor being configured to compute an estimate value of the playback SPL.

3. The system of claim 2, wherein the playback signal combines a plurality of sound sources, the processor being configured to compute an estimate specific SPL for each of the sound sources and to process each of the plurality of sound sources according to the model of the transfer function between the IEM and the IELS.

4. The system of claim 1, wherein the at least one specific SPL is a residual ambient SPL, the processor being configured to compute an estimate value of the residual ambient SPL using the model of the transfer function between the IEM and the OEM and the ambient sound captured by the OEM.

5. The system of claim 1, wherein the processor is further configured to compute a correction for each of the at least one estimated specific SPL.

6. The system of claim 1, wherein the at least one model of the transfer function is an adaptive digital filter.

7. The system of claim 1, wherein the HPD further comprises a digital sound processor configured to receive the playback signal as input.

8. The system of claim 4, the processor being further configured to compute an OEM A-weighting according to the ambient sound captured by the OEM and to compute an estimated residual ambient A-weighting according to the estimated residual ambient SPL.

9. The system of claim 8, wherein the processor is further configured to compute a personal attenuation rating (PAR) estimate by subtracting the estimated residual ambient A-weighting from the OEM A-weighting.

10. The system of claim 1 further comprising a diagnostic module configured to receive the at least one estimated specific SPL.

11. A system to measure noise reduction and evaluate contributions of various sound sources to a sound dose, the system comprising:
    a hearing protection device (HPD) comprising:
        a passive attenuation device adapted to reduce ambient sound present outside an ear of a wearer of the HPD;
        an inner ear microphone (IEM) adapted to capture a general sound pressure level (SPL) of the sound dose present in the ear canal;
        at least one of an outer ear microphone (OEM) adapted to capture the ambient sound; and
        an in-ear loudspeaker (IELS) configured to emit a playback signal in an ear canal of a wearer according to at least one sound source;
    a processor in signal communication with the IEM and with at least one of the OEM and the IELS, the processor being configured to:

estimate at least one specific SPL corresponding to an identified sound component of the sound dose in the ear canal using at least one model of a transfer function between the IEM and at least one of the OEM and the IELS; and compute a correction for each of the at least one estimated specific SPL.

12. The system of claim 6, wherein the plurality of sound sources is at least one of an audio signal, a communication signal or a level-controlled output of the OEM.

13. The system of claim 11, wherein the diagnostic module is configured to recommend at least one action to be executed by the wearer to reduce the sound dose in the ear canal.

14. The system of claim 13, wherein the diagnostic module triggers an audio processing algorithm to automatically reduce specific in-ear SPL caused by one or more of the sound sources.

15. A system to measure noise reduction and evaluate contributions of various sound sources to a sound dose, the system comprising:

a hearing protection device (HPD) comprising:

a passive attenuation device adapted to reduce ambient sound present outside an ear of a wearer of the HPD;

an inner ear microphone (IEM) adapted to capture a general sound pressure level (SPL) of the sound dose present in the ear canal;

at least one of an outer ear microphone (OEM) adapted to capture the ambient sound; and an in-ear loudspeaker (IELS) configured to emit a playback signal in an ear canal of a wearer according to at least one sound source;

a processor in signal communication with the IEM and with at least one of the OEM and the IELS, the processor being configured to:

estimate at least one specific SPL corresponding to an identified sound component of the sound dose in the ear canal using at least one model of a transfer function between the IEM and at least one of the OEM and the IELS; and compute a correction for each of the at least one estimated specific SPL.

* * * * *